United States Patent
Hu et al.

(10) Patent No.: US 10,980,410 B1
(45) Date of Patent: Apr. 20, 2021

(54) VIDEO TOOTHBRUSH

(71) Applicant: SHENZHEN WILLSEA E-COMMERCE CO. LIMITED, Shenzhen (CN)

(72) Inventors: Wentao Hu, Shenzhen (CN); Zhenjie Mo, Shenzhen (CN)

(73) Assignee: SHENZHEN WILLSEA E-COMMERCE CO. LIMITED, Shenzhen (CN)

( * ) Notice: Subject to any disclaimer, the term of this patent is extended or adjusted under 35 U.S.C. 154(b) by 0 days.

(21) Appl. No.: 16/848,794

(22) Filed: Apr. 14, 2020

Related U.S. Application Data

(63) Continuation of application No. PCT/CN2020/076651, filed on Feb. 25, 2020.

(51) Int. Cl.
 *A61B 1/24* (2006.01)
 *A46B 15/00* (2006.01)
 (Continued)

(52) U.S. Cl.
 CPC .............. *A61B 1/24* (2013.01); *A46B 9/04* (2013.01); *A46B 13/02* (2013.01);
 (Continued)

(58) Field of Classification Search
 CPC ....... A61C 17/22; A61C 17/221; A61C 17/24; A61C 17/26; A61C 17/32; A61C 17/34;
 (Continued)

(56) References Cited

U.S. PATENT DOCUMENTS

| 6,685,471 B1 * | 2/2004 | Kawamura ........ A46B 15/0002 |
| | | 15/105 |
| 8,938,838 B2 * | 1/2015 | Vashi .................. A46B 5/0095 |
| | | 15/106 |

(Continued)

FOREIGN PATENT DOCUMENTS

| CN | 101797187 A | 8/2010 |
| CN | 102342864 A | 2/2012 |

(Continued)

OTHER PUBLICATIONS

Computer generated English translation of WO 2012/108642 A2, Lim, Jeong Seon, published Aug. 16, 2012. (Year: 2012).*

(Continued)

*Primary Examiner* — Laura C Guidotti
(74) *Attorney, Agent, or Firm* — Bayes PLLC

(57) ABSTRACT

Embodiments of the disclosure provide a video toothbrush. An exemplary video toothbrush may include a handle housing an exciter and a support element including a support neck and a support head. The support element may be configured to extend from a proximal connection with the handle to a distal end. The video toothbrush may further include a camera mounted near the distal end of the support head and a shaft extending from the support neck and configured to support a cleaning head toward a distal end of the shaft and configured to receive vibration from the exciter toward a proximal end of the shaft. The video toothbrush may also include the cleaning head having a plurality of (Continued)

bristles projecting in a first direction. The cleaning head may define a central opening. The central opening may be arranged to provide the camera with a view in the first direction.

20 Claims, 11 Drawing Sheets

(51) Int. Cl.
| | |
|---|---|
| *A46B 13/02* | (2006.01) |
| *A61B 1/06* | (2006.01) |
| *A61B 1/00* | (2006.01) |
| *A61B 1/12* | (2006.01) |
| *A61C 17/34* | (2006.01) |
| *A46B 9/04* | (2006.01) |
| *A46B 13/00* | (2006.01) |
| *A46B 5/00* | (2006.01) |

(52) U.S. Cl.
CPC ...... *A46B 15/0036* (2013.01); *A46B 15/0055* (2013.01); *A61B 1/00011* (2013.01); *A61B 1/00193* (2013.01); *A61B 1/0684* (2013.01); *A61B 1/127* (2013.01); *A61C 17/3436* (2013.01); *A61C 17/3445* (2013.01); *A46B 5/0095* (2013.01); *A46B 13/008* (2013.01); *A46B 15/0022* (2013.01); *A61C 2204/002* (2013.01)

(58) Field of Classification Search
CPC ............ A61C 17/3409; A61C 17/3427; A61C 17/3436; A61C 17/3445; A61C 17/3454; A61C 17/3463; A61C 17/3472; A61C 17/3481; A61C 2204/00; A61C 2204/002; A46B 13/02; A46B 15/0004; A46B 15/0055; A46B 2200/1066; A46B 9/04; A61B 1/24; A61B 1/247; A61B 1/253; A61B 1/127; A61B 1/0684
See application file for complete search history.

(56) References Cited

U.S. PATENT DOCUMENTS

| | | | |
|---|---|---|---|
| D795,419 S | 8/2017 | Kohler | |
| D832,421 S | 10/2018 | Kohler | |
| D832,422 S | 10/2018 | Kohler | |
| D836,777 S | 12/2018 | Kohler | |
| 10,646,314 B2 * | 5/2020 | Zhou | ........................ A46B 9/04 |
| 2015/0107034 A1 * | 4/2015 | Shani | ................ A46B 15/0006 15/22.1 |
| 2015/0230595 A1 | 8/2015 | Vila | |
| 2015/0257636 A1 * | 9/2015 | Kohler | .................. A61C 15/02 433/29 |
| 2016/0037903 A1 | 2/2016 | Lal | |
| 2020/0222160 A1 * | 7/2020 | Zhou | ..................... A61B 1/247 |

FOREIGN PATENT DOCUMENTS

| | | | | |
|---|---|---|---|---|
| CN | 203195788 U | 9/2013 | | |
| CN | 106562558 A | 4/2017 | | |
| CN | 107049539 A | 8/2017 | | |
| WO | 2012108642 A2 | 8/2012 | | |
| WO | WO 2012/108642 A2 * | 8/2012 | ............ | A46B 15/00 |
| WO | 2013001462 A2 | 1/2013 | | |
| WO | 2019072018 A1 | 4/2019 | | |

OTHER PUBLICATIONS

International Search Report issued in corresponding International Application No. PCT/CN2020/076651, dated Oct. 27, 2020, 4 pages.

Written Opinion of the International Searching Authority issued in corresponding International Application No. PCT/CN2020/076651, dated Oct. 27, 2020, 4 pages.

* cited by examiner

VIDEO TOOTHBRUSH

CROSS-REFERENCE TO RELATED APPLICATION

The present application is a bypass continuation of International Patent Application No. PCT/CN2020/076651, filed on Feb. 25, 2020, the entire contents of which are expressly incorporated herein by reference.

TECHNICAL FIELD

The present disclosure relates to systems and methods for a video toothbrush, such as a toothbrush with a video camera aligned with bristles or other cleaning elements and configured to provide a live video output for brushing quality enhancement or other purposes.

BACKGROUND

The field of toothbrushes has been filled with innovations since the 1400s. In the last half century, electric toothbrushes have been introduced. Today, toothbrushes continue to incorporate further technological innovations.

Recently there have been attempts to incorporate video into electric toothbrushes to provide video electric toothbrushes. These attempts have been mainly unsuccessful for a variety of reasons. For example, certain toothbrushes have incorporated video as a secondary feature, such that a user can take a video image of the user's own teeth at a first time, and brush the user's teeth at a second time. Other approaches may permit video images of the user's teeth during brushing, but can only do so from an odd or confusing angle.

Embodiments of the disclosure address the above problems by providing improved video toothbrush systems, which may have a video camera aligned with bristles or other cleaning elements and configured to provide a live video output for brushing quality enhancement and improved user experience. Furthermore, certain embodiments of the disclosure reduce the mouth impact of the video toothbrush, permitting ease of simultaneous brushing and video observation, as well as ease of insertion into the mouth of the user.

SUMMARY

Embodiments of the disclosure provide an apparatus that may include a handle housing an exciter. The apparatus may also include a support element including a support neck and a support head. The support element may be configured to extend from a proximal connection with the handle to a distal end. The apparatus may further include a camera mounted near the distal end of the support head. The apparatus may additionally include a shaft extending from the support neck and configured to support a cleaning head toward a distal end of the shaft and configured to receive vibration from the exciter toward a proximal end of the shaft. The apparatus may also include the cleaning head having a plurality of bristles projecting in a first direction. The cleaning head may define a central opening. The central opening may be arranged to provide the camera with a view in the first direction.

Embodiments of the disclosure also provide a further apparatus that may include a handle with an exciter. The apparatus may also include a support element including a support neck and a support head. The support element may be configured to extend from a proximal connection with the handle to a distal end. The apparatus may further include a camera mounted near the distal end of the support head. The apparatus may additionally include a shaft extending from the support neck and configured to support a cleaning head toward a distal end of the shaft and configured to receive vibration from the exciter toward a proximal end of the shaft. The camera may be configured to view through a central opening of the cleaning head upon installation of the cleaning head.

It is to be understood that both the foregoing general description and the following detailed description are exemplary and explanatory only and are not restrictive of the invention, as claimed.

DETAILED DESCRIPTION

Certain embodiments of the present disclosure provide a video toothbrush. For example, certain embodiments provide a toothbrush that can obtain video of dental cleaning during the cleaning process. In an example, a camera can be provided behind vibrating bristles, which may permit the simultaneous cleaning of teeth and monitoring of the surface status of the teeth being cleaned. Certain embodiments provide vibration isolation or dampening, which may improve the quality of video captured by the toothbrush or reduce the performance requirements of an embedded camera or processor.

For example, a camera with a frame capture speed sufficiently fast may be unaffected by vibrations of the toothbrush. Nevertheless, such high-speed cameras may have other limitations, such as cost, complexity, and/or bulk. Likewise, vibration interference may be resolved by suitable image processing techniques, such as image stabilization. Nevertheless, to perform such stabilization in real time in the presence of a highly unstable camera may require significant computational power, which may lead to additional cost, complexity, and/or bulk.

The camera of certain embodiments may be co-axially aligned with a brushing head and have a clearance for isolating vibration. The clearance may be sufficiently narrow to reduce the bulkiness and permit easy handling of the toothbrush.

Figure 1:
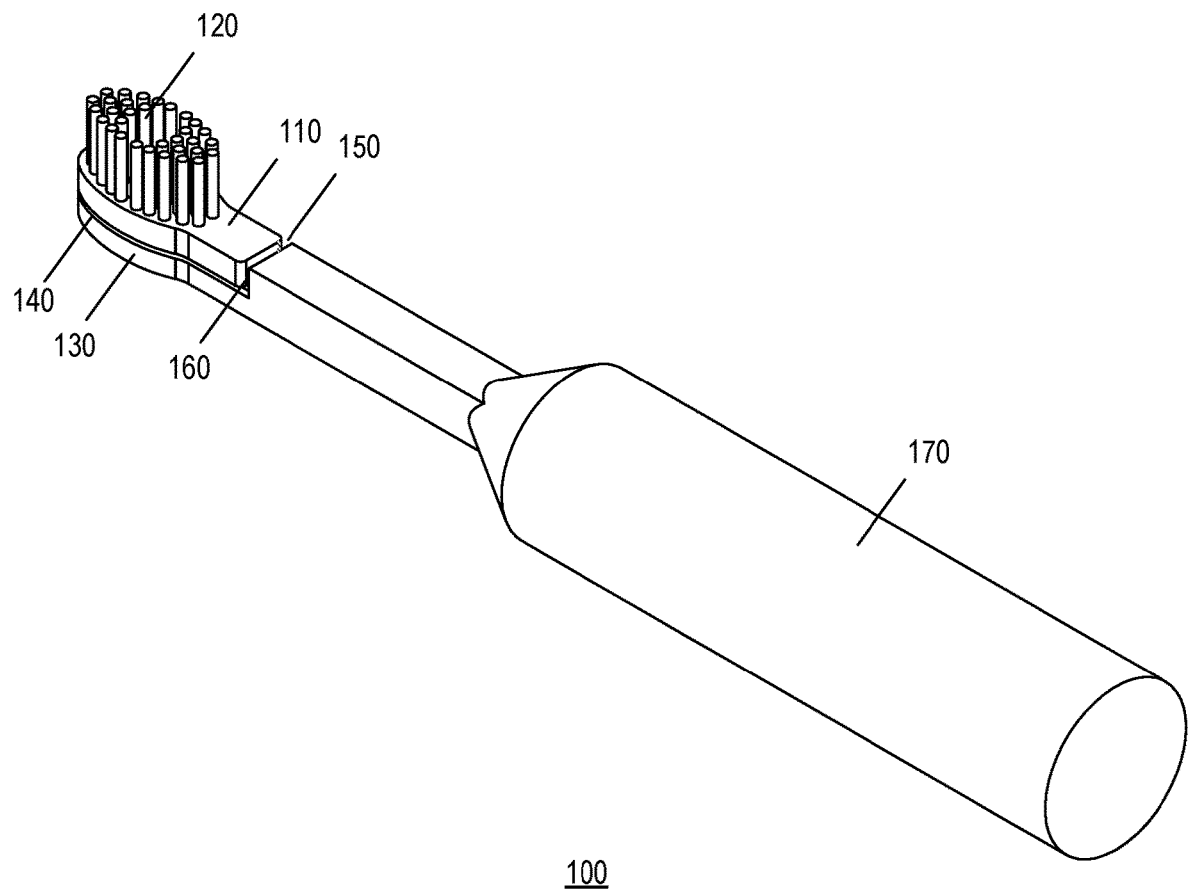
FIG. 1 illustrates a perspective view of a video toothbrush, according to certain embodiments.

FIG. 1 illustrates a perspective view of a video toothbrush according to certain embodiments. As shown in FIG. 1, a device 100 can include a handle 170 and a cleaning head 110 with bristles 120. Device 100 can also include a support head 130 separated from the cleaning head 110 by first clearance 140 in the vertical direction and separated from the cleaning head 110 by second clearance 150 in the horizontal direction. First clearance 140 may be between 0.5 mm to 5 mm. For example, first clearance 140 may be 0.5 mm, 1 mm, 1.5 mm, 2 mm, 2.5 mm, 3 mm, 3.5 mm, 4 mm, 4.5 mm, 5 mm, or within any range defined by the above-listed values. Second clearance 150 may be between 0.5 mm to 5 mm. For example, second clearance 150 may be 0.5 mm, 1 mm, 1.5 mm, 2 mm, 2.5 mm, 3 mm, 3.5 mm, 4 mm, 4.5 mm, 5 mm, or within any range defined by the above-listed values. In certain embodiments, the direction toward the cleaning head 110 may be considered the distal direction, while the direction toward handle 170 may be considered the proximal direction.

Cleaning head 110 may be supported by shaft 160, which may extend along the horizontal direction inside support head 130. Shaft 160, which is obscured from the angle shown in FIG. 1 but passes through second clearance 150, may be configured to transfer vibrations from a motor inside handle 170 to the cleaning head 110. Shaft 160 may also be configured to support cleaning head 110 when bristles 120 are pressed against teeth (not shown). A camera, not visible in this view, may be provided in support head 130. Wires for the camera may run inside support head 130 and connect to processors, transmitters, receivers, and the like, inside handle 170.

Handle 170 may be sealed and waterproofed. For example, handle 170 may be configured to resist water according to ingress protection (IP) code 7, which may indicate that harmful quantities of water cannot enter the enclosure when the enclosure is immersed in water of up to 1 meter depth for at least a few minutes. In some embodiments, higher IP ratings (e.g., IP code 8) or lower IP ratings (e.g., IP code 6) may be used, depending on the requirements of particular applications. Other levels of water resistance or water proofing are also permitted. The IP codes are published by the International Electrotechnical Commission (IEC) and described at IEC standard 60529 with a corresponding European standard EN 60529.

Figure 2:
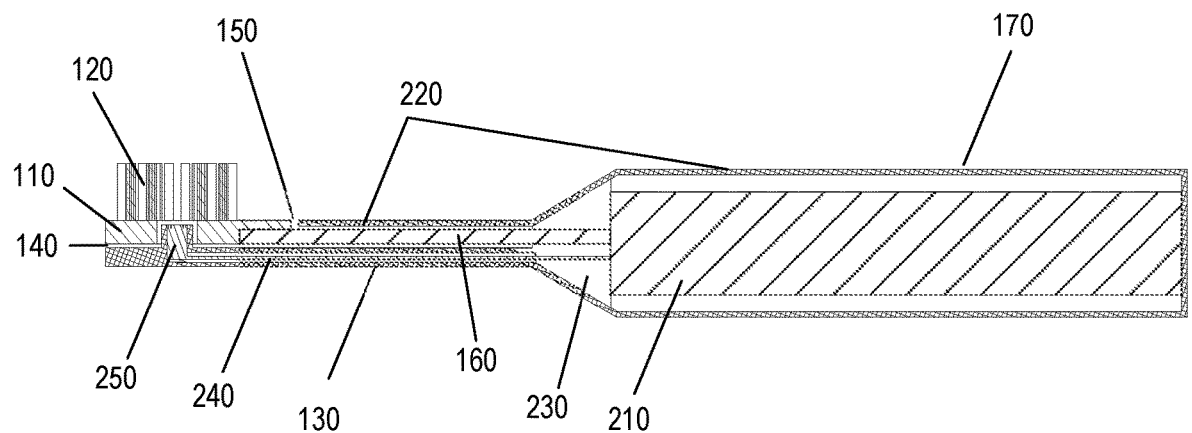
FIG. 2 illustrates a vertical cross-section of a video toothbrush, according to certain embodiments.

FIG. 2 illustrates a vertical cross-section of a toothbrush according to certain embodiments. As shown in FIG. 2, shaft 160 may link motor 210 to cleaning head 110. Handle 170 can be formed from an outer housing 220, annular spacer 230, and a compartment for motor 210. The compartment housing motor 210 may also include (not shown) a control circuit board, a wireless transmission module, one or more battery, or the like. Also not shown, the housing 220 may include one or more port, such as an electric power port for charging and/or a universal serial bus (USB) port for wired communication and/or charging. In some embodiments, a coil may be provided for wireless charging. Other ports are also permitted.

Cabling 240 may connect the compartment housing motor 210 to a camera 250. Cabling 240 can include power and signaling wires. The camera 250 may be provided with an illumination source, such as one or more light emitting diodes (LEDs). In FIG. 2, camera 250 and LEDs are shown as a single bundle, but they may be scattered. For example, multiple LEDs may be arranged in a circular pattern around the periphery of an end of the toothbrush, while camera 250 itself may be centered. Nevertheless, in certain embodiments, the LEDs may be located immediately adjacent to and in approximately the same plane as a lens of camera 250.

In certain embodiments, the camera may be located in handle 170 and fiber optics may be provided so that the camera can view directly out of the support head 130 through the fiber optics.

Cleaning head 110 may be separable from or integral with shaft 160. Likewise, shaft 160 may be permanently installed or may be removable. Thus, for example, in certain embodiments the clean head 110 may be removable/replaceable or both the cleaning head 110 and the shaft 160 may be removable/replaceable.

Figure 3:
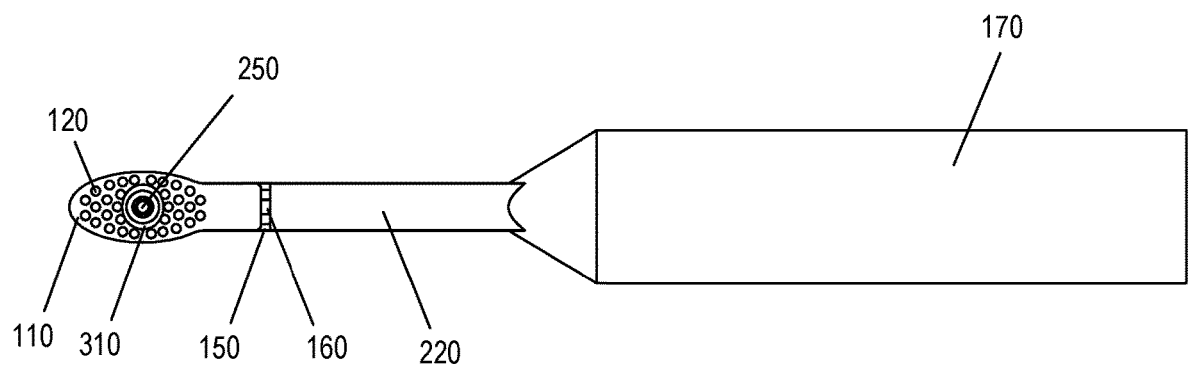
FIG. 3 illustrates aside view of a video toothbrush, according to certain embodiments.

FIG. 3 illustrates a side view of a video toothbrush according to certain embodiments. The view of FIG. 3 may be orthogonal to the view of FIG. 2. As shown in FIG. 3, the housing 220 can extend from the handle 170. Second clearance 150 can separate the cleaning head 110 from the housing 220, while shaft 160 can bridge second clearance 150 and provide vibrational motion to the cleaning head 110 and bristles 120.

As also shown in FIG. 3, a third clearance 310 may be an annular gap between a casing of camera 250 and cleaning head 110. Third clearance 310 may be obtained by providing a circular opening in cleaning head 110. In certain embodiments, the shape of third clearance 310 may be adjusted to an oval or rounded rectangle, to permit clearance to be present as the cleaning head 110 reciprocates in the left-right direction.

Figure 4:
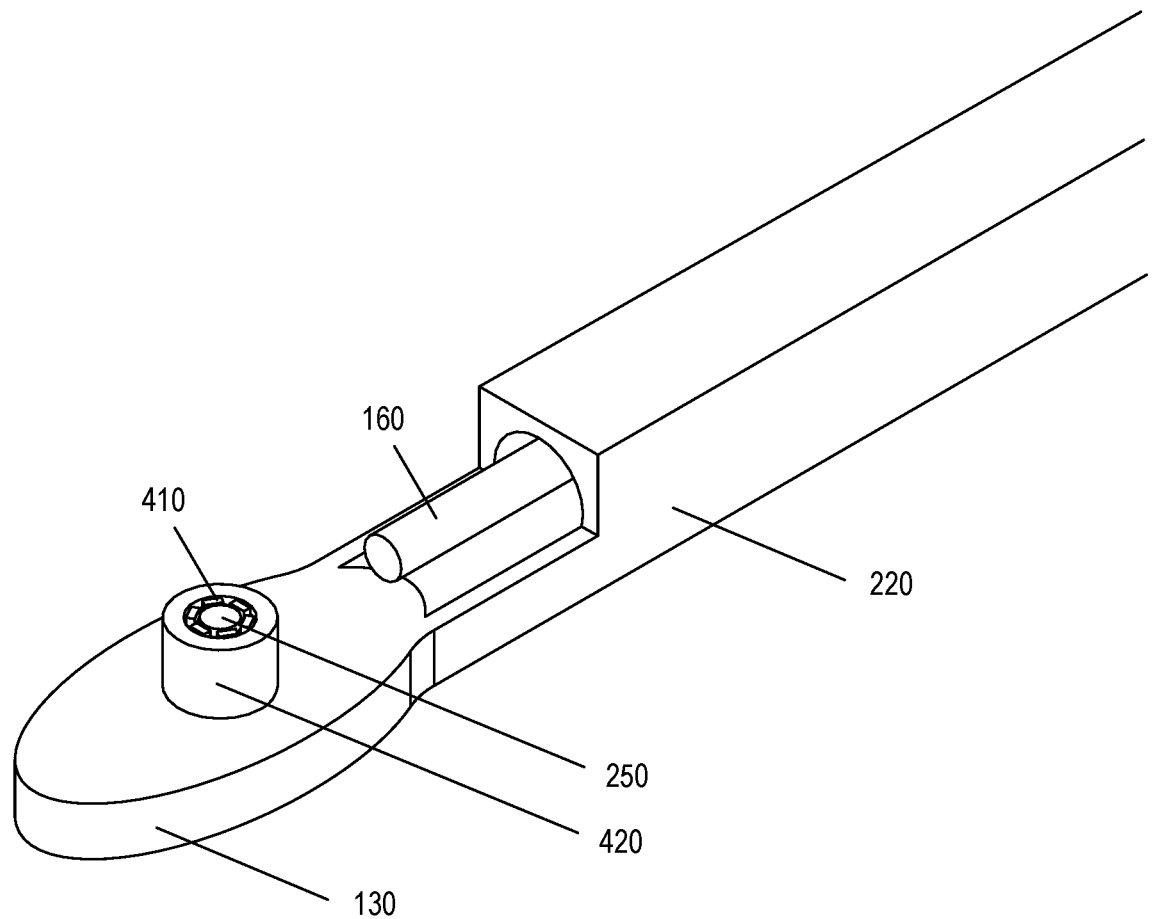
FIG. 4 illustrates a perspective view of a video toothbrush without a cleaning head, according to certain embodiments.

FIG. 4 illustrates a perspective view of a video toothbrush without a cleaning head, according to certain embodiments. As mentioned above, in certain embodiments the cleaning head may be removed. FIG. 4 illustrates such an embodiment. In the embodiment of FIG. 4, the shaft 160 has not been removed. An end of shaft 160 may be a simple cylinder as shown, or may be provided with a strip, a detent mechanism, threads, a ball or socket, or other mechanism configured to permit non-destructive attachment and removal of the cleaning head.

As shown in FIG. 4, camera 250 can be surrounded by adjacent LEDs 410. In this case, six LEDs 410 are shown, although other numbers of LEDs 410 are permitted. The LEDs 410 may emit light having any desired wavelength. In certain embodiments, blue or ultraviolet (UV) LEDs 410 may be used to provide illumination of dental surfaces and/or to help highlight a contrast agent such as a plaque disclosing tablet. An example of such a disclosing agent is Erythrosine, which may appear black under blue light.

As also shown in FIG. 4, camera 250 and LEDs 410 may be mounted inside a casing 420. Casing 420 can be integral with support head 130, which may also be integral with housing 220. Thus, for example, casing 420, support head 130, and housing 220 may be formed as a single continuous piece.

In FIG. 4, camera 250 is illustrated as being mounted at about the same level as shaft 160. Other arrangements are also possible, such as mounting the camera at a position higher than shaft 160 (and consequently closer to target teeth of a user) or at a position lower than shaft 160 (and consequently farther from the target teeth).

Shaft 160 is shown as extending approximately through a central axis of housing 220, although other arrangements are also possible.

The arrangement of FIGS. 1 through 4 may be viewed of as an example of a floating cleaning head embodiment. In this approach, the cleaning head would have no or only slight contact with camera casing, the support head, or the housing of the handle under regular use scenarios. For example, shaft 160 and cleaning head 110 may be sufficiently rigid such that clearance 140 can be substantially maintained during the cleaning process. In another example, the back surface of cleaning head 110 and/or the front surface of support head 130 that defines clearance 140 may be coated with a low-friction material to allow free or low-friction movement of cleaning head 110 relative to support head 130 even when they contact each other under external pressure. Further modifications are also possible.

Figure 5:
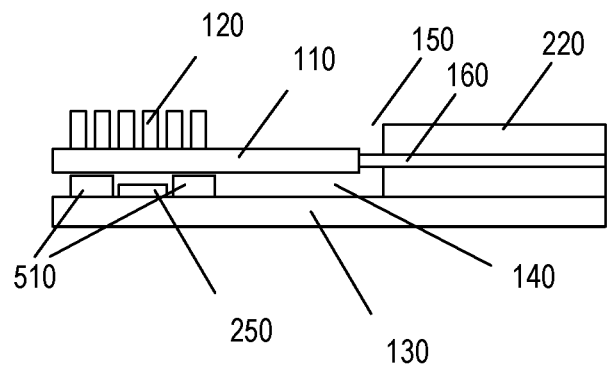
FIG. 5 illustrates a video toothbrush with bumpers, according to certain embodiments.

FIG. 5 illustrates a video toothbrush with bumpers according to certain embodiments. As shown in FIG. 5, cleaning head 110 can be separated from housing 220 by second clearance 150 and separated from support head 130 by first clearance 140. In addition, one or more bumpers 510 can be provided. Bumpers 510 may be provided as a pair of lines or a ring around camera 250. Bumpers 510 may be configured to prevent cleaning head 110 from being deflected into contact with camera 250 during use. For example, as bristles 120 press against a user's teeth, the cleaning head 110 may be forced in a downward direction toward support head 130. Bumpers 510 may limit motion of the cleaning head 110 in this direction. Bumpers 510 can be formed from a material that limits transmission of vibration between the cleaning head 110 and support head 130.

In some embodiments, a video toothbrush can be provided with a port configured to allow one or more battery to be inserted or removed. The video toothbrush can also be provided with a communication module that is configured to permit transfer of images from the camera to a display remote from the video toothbrush. For example, a USB port may be used to transfer video data over a wired connection from the video toothbrush to a smart phone. Similarly, Bluetooth and/or wireless network (e.g., WiFi) communication equipment, including an antenna, may be included and may be configured to wirelessly transmit video data to a smart phone or other display.

In the above discussion a motor is identified as a possible exciter to transmit motion through a shaft to the cleaning head. Other exciters are also possible, including machines that convert hand pumping into vibrational motion, or piezoelectric translators/transducers.

The camera can be configured with one or more lenses. An outermost lens may be coated with an anti-fog surface treatment, such as a layer comprising titanium dioxide. In certain embodiments, the anti-fog capabilities of the titanium dioxide may be enhanced by the use of at least one UV LED. Other hydrophilic layers configured to limit fogging may also be used. The lens may be configured to provide a desired image and may be a macro lens, a fish-eye lens, or any other suitable lens. For example, the lens may have a short focus length (e.g., a macro lens) to be able to focus on the surface of the teeth that is about 1 centimeter or less in distance from the lens. In another example, the lens may have a wide field of view to cover a relatively large area of the teeth being cleaned. In certain embodiments, two or more cameras may be employed in a side-by-side configuration to provide stereoscopic images.

In some embodiments, additional vibration remediation techniques can be employed. For example, the support head may include vibration dampening materials or vibration dampening structures, such as mechanical joints, rubber, foam, or combinations thereof. For example, the annular spacer 230 may be made from a material that dampens vibrations.

In some embodiments, external ports may be provided to permit charging of the device. Alternatively or additionally, battery compartment doors may be provided to permit replacement of the batteries. In certain embodiments, batteries and/or super capacitors may be configured for wireless recharging. For example, the video toothbrush may be provided with a stand that permits air drying of the bristles and wireless charging of the toothbrush.

The various views of the above-described embodiment do not explicitly show a power button. In certain embodiments a power button may be provided on the handle of the video toothbrush. In some embodiments, activation of the video toothbrush may be performed by a remote device, such as a smart phone.

Figure 6:
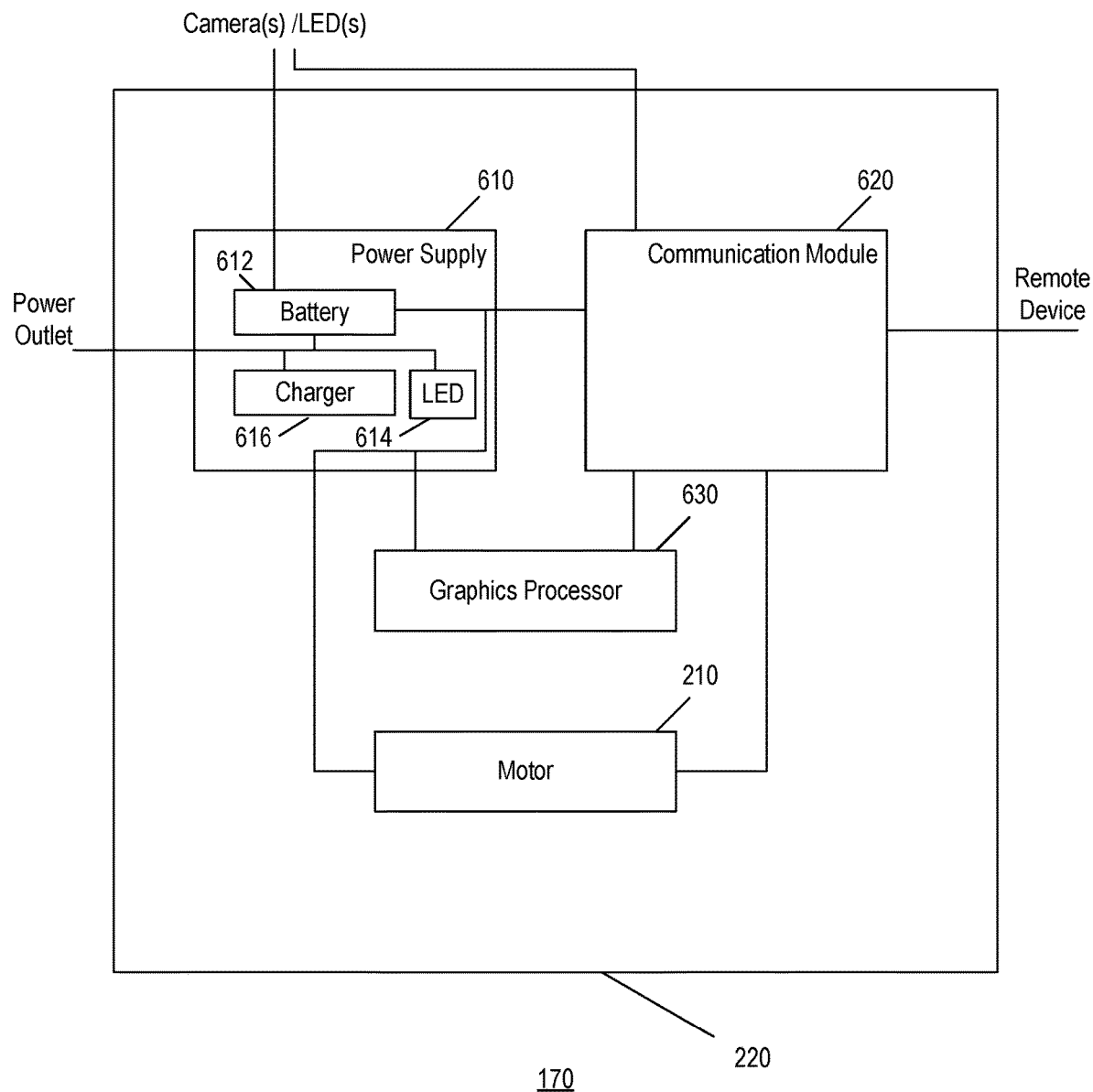
FIG. 6 illustrates a functional block diagram of a handle of a video toothbrush handle, according to certain embodiments.

FIG. 6 illustrates a functional block diagram of handle 170 of a video toothbrush, according to certain embodiments. As shown in FIG. 6, housing 220 may house not only motor 210, but also other components. For example, a power supply 610 can be provided including a battery 612, status LED 614, and charger 616. The power supply 610 can be connected to an external power outlet and can supply power to the camera(s)/LED(s) of the head of the toothbrush. The power supply 610 can also power a communication module 620, graphics processor 630, and a motor 210 within the housing. The communication module 620 can communicate data with the camera(s)/LED(s) of the head of the toothbrush, can provide instructions to motor 210 of the toothbrush, and can communicate data and control signals with a remote device, such as a smart phone. The communication module 620 may thus provide a communication interface to the remote device over which commands, data, and the like may be provided. The graphics processor 630 may be used for video image acquisition and/or processing, such as image stabilization, image compression, or other features. Other elements may also be included within the housing including, for example, memory, a timer, a speaker for providing an audible alarm or instruction, a user interface display, buttons, or the like. Additional sensors can be provided, include motion sensors, ranging sensors, and the like. The motion sensors and/or ranging sensors may be used to aid in determination of a current position of the video toothbrush. Sensor data can be passed to the remote device together with camera data.

In some embodiments, the video toothbrush may include a toothpaste dispenser configured to deliver toothpaste to the bristles. This dispenser may be refillable or may be a disposable portion of the replaceable cleaning head. In some embodiments, the toothpaste may be foamless to aid video capture.

Figure 7:
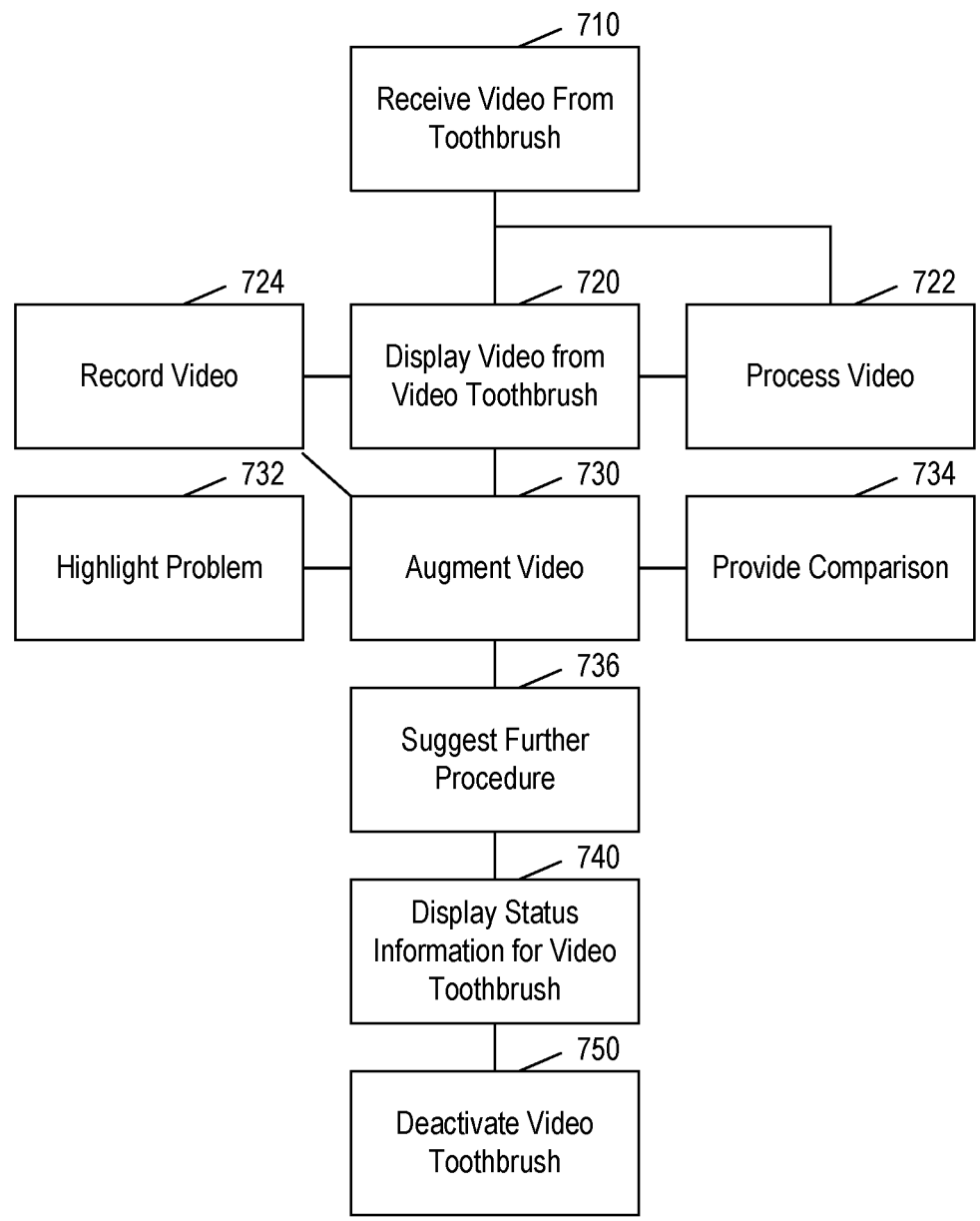
FIG. 7 illustrates a method of operation of an exemplary video toothbrush, according to certain embodiments.

FIG. 7 illustrates a method 700 according to certain embodiments. Method 700 may be performed by, for example, a smart phone or other device remote from the video toothbrush. For example, a display installed in or behind a bathroom mirror surface could be used. Certain steps of method 700 may also be performed, at least partially, by toothbrush 100. Method 700 may include a plurality of steps, as shown in FIG. 7. In some embodiments, one or more steps shown in FIG. 7 may be omitted, or one or more additional steps may be added to method 700. The steps of method 700 may be performed in different order from that shown in FIG. 7, and some steps may be performed simultaneously.

As shown in FIG. 7, method 700 can begin, at step 710, with receiving video from a video toothbrush (e.g., video toothbrush 100). The video toothbrush may be activated to capture and transmit video signals. This may be performed via a user pressing a button or moving a switch on the video toothbrush. In some embodiments, the activation can be performed using a smart phone or other remote device. In certain embodiments, activating the video toothbrush can involve activating movement of the bristles only, activating video only, or activating both movement and video. After activation, video of the surface of teeth can be captured by, for example, camera 250, processed by graphics processor 630, and transmitted by communication module 620. A remote device such as a smart phone may receive the video signals via wired or wireless connections to the video toothbrush through, for example, communication module 620.

At step 720, video received from the video toothbrush can be provided on a display, such as on the screen of a smart phone.

In some embodiments, prior to displaying the video at step 720, a device may process the video at step 722. This video processing may be performed in the video toothbrush, at a remote device, such as a smartphone, or distributed between the video toothbrush and a remote device. The video processing may include aspects such as image stabilization or other enhancements.

Method 700 can also include, at step 730, augmenting the video. For example, at step 732, the method can include highlighting a problem. To highlight a problem, the remote device and/or the video toothbrush (hereinafter referred to as a system) may analyze a received video image for the presence of plaque or debris. The system may then highlight the presence of such plaque or debris, so that the video toothbrush can be controlled to address the highlighted issue. At step 734, the system may provide a comparison video or comparison still image. This may include a reference, such as an historical image or video, or a tutorial image or video. For example, the system can record video at step 724 and subsequently use the recorded video to augment live video at step 730 by providing a comparison at step 734. Motion and/or ranging sensors may be used to permit comparison between a currently captured image and an historical image. The comparison at step 734 may include a comparison of whiteness of teeth, for example by comparing an average whiteness of recent images of a tooth with average whiteness of historical images of the tooth.

Method 700 may also include, at step 736, suggesting a further procedure. For example, the system can analyze the video and determine areas that have not been cleaned yet or that have not been adequately cleaned. Thus, the system may provide a text-based suggestion, such as, "Don't forget to brush your molars!" or may provide a visual guide, such as pointing to an area that requires cleaning. In case the video toothbrush is being controlled robotically, the system can instruct the robot where to clean next, rather than merely providing a suggestion.

Method 700 may also include, at step 740, displaying status information for the video toothbrush. The status information may include information such as a current charge level of the video toothbrush, a connectivity quality between the video toothbrush and the remote device, any fault conditions experienced by the video toothbrush, a current number of uses or hours of usage of a given cleaning head, or a level of toothpaste in a dispenser. The system may be configured to prompt reordering or automatically reorder cleaning head(s) and/or toothpaste for a user of the video toothbrush.

At step 750, method 700 can include deactivating the video toothbrush. Such deactivation can involve placing the video toothbrush in a low power mode, such that it can be re-activated remotely, or completely powering off the video toothbrush.

Embodiments of the present disclosure may provide certain benefits and/or advantages. For example, certain embodiments may permit a user to look where the user is brushing, from approximately the same vantage point as the bristles. This may permit the user to accurately ascertain whether all tooth surfaces are being adequately and thoroughly cleaned, which may promote oral health and/or hygiene.

Figure 8:
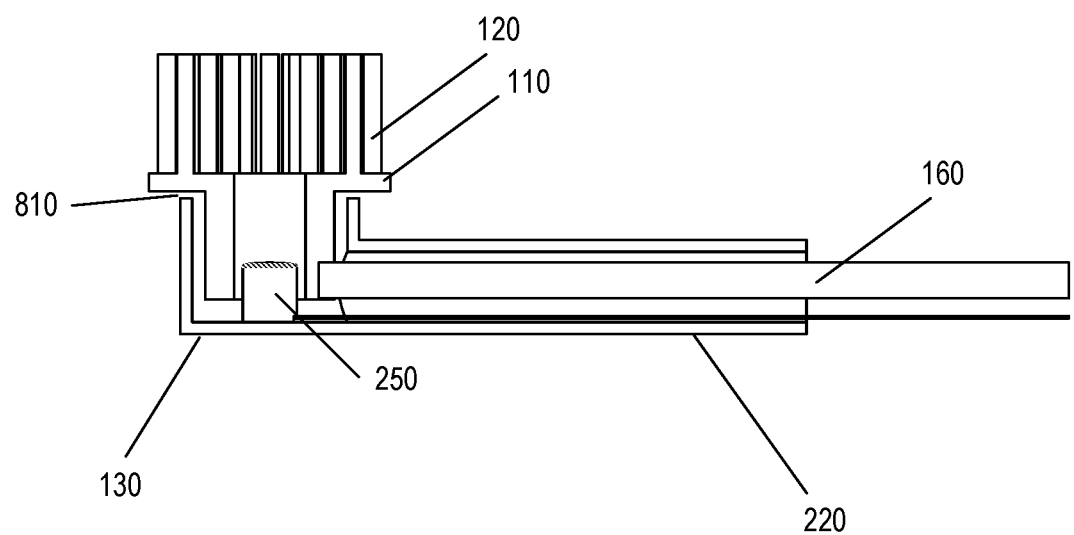
FIG. 8 illustrates a video toothbrush with a rotating cleaning head, according to certain embodiments.

FIG. 8 illustrates a video toothbrush with a rotating cleaning head, according to certain embodiments. The embodiment of FIG. 8 may have many homologous structures to those shown in FIGS. 1-6. Accordingly, where it is convenient for ease of reference the same reference numbers may be used.

In the embodiment shown in FIGS. 1-5, it is assumed that the cleaning head 110 may move or translate in an approximately linear reciprocating motion. By contrast, in FIG. 8, the cleaning head 110 may move in a continuous or reciprocating rotational direction. In both embodiments, the cleaning head 110 may have a central open area through which camera 250 may view. In both embodiments, the camera 250 may be affixed to a support head 130, which may be integral with a housing 220. In both embodiments, a shaft 160 may transmit energy from an exciter, such as a motor, in a handle of the video toothbrush.

In the embodiment of FIG. 8, there may be an outer clearance 810 between the cleaning head 110 and the housing 220. Additionally, there may be bearings or similar features within the end of the video toothbrush, as the cleaning head 110 may comprise a roughly top-hot shaped member, with a cylindrical wall and a disk shaped brim from which the bristles 120 extend. The bearings, if used, may help to support and separate the cleaning head 110 from the housing 220. The housing 220 at the cleaning end of the video toothbrush may function as the support head 130.

Figure 9:
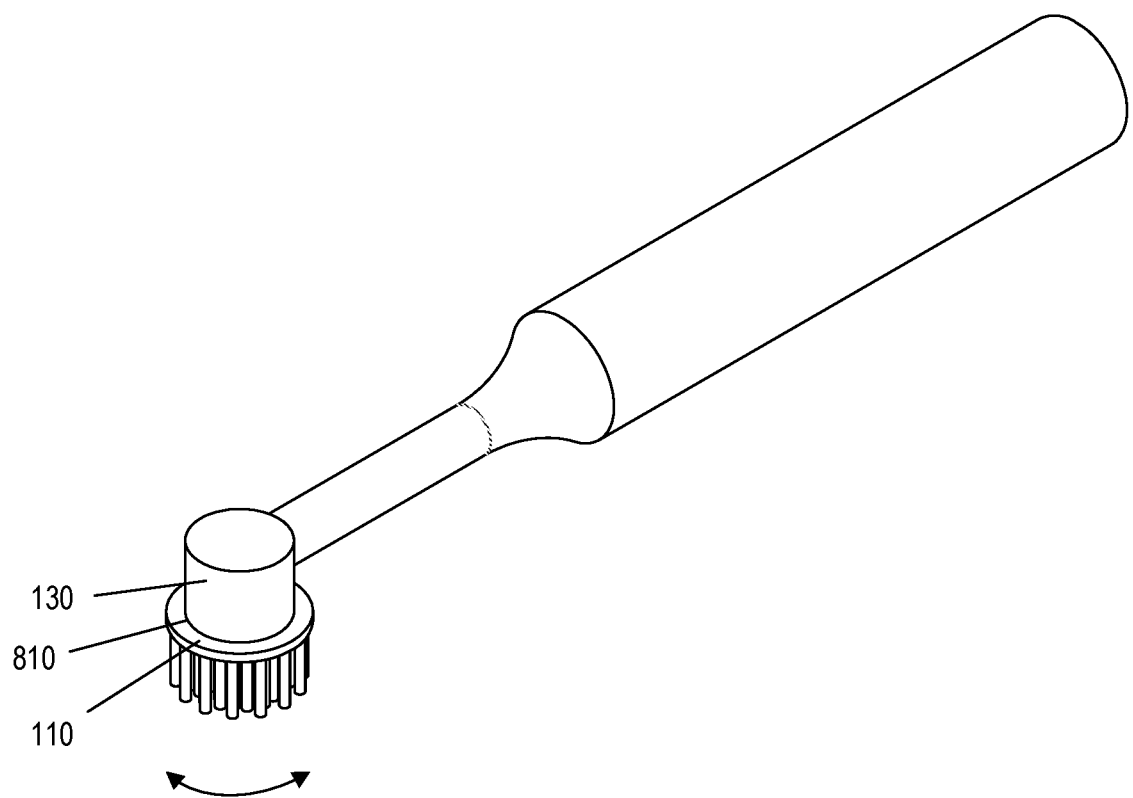
FIG. 9 illustrates a perspective view of a video toothbrush with a rotating cleaning head, according to certain embodiments.

FIG. 9 illustrates a video toothbrush with a rotating cleaning head, according to certain embodiments. FIG. 9 can be considered as a perspective view of the embodiment shown in FIG. 8. As shown in FIG. 9, the cleaning head 110 can rotate, while the support head 130 may remain static and separated by clearance 810.

In the embodiments shown in FIGS. 8 and 9, clearance 810 may be small (for example, less than 5 mm, 2 mm, 1 mm, etc.), and cleaning head 110 may be configured to glide along the surface of support head 130 if contact is made between cleaning head 110 and support head 130.

Figure 10:
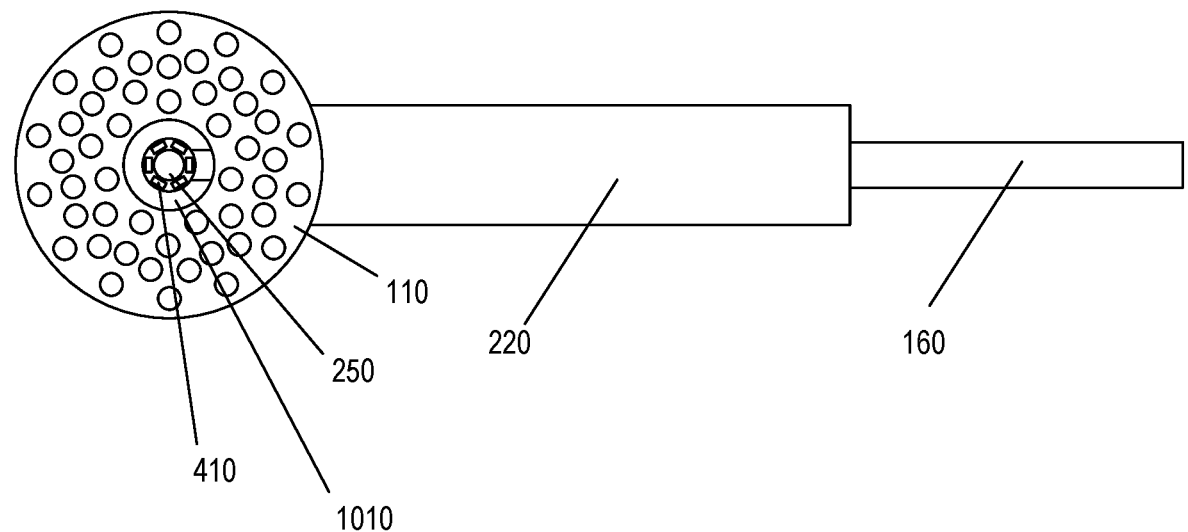
FIG. 10 illustrates a side view of a video toothbrush, according to certain embodiments.

FIG. 10 illustrates a side view of a video toothbrush according to certain embodiments. The embodiment of FIG. 10 can be considered as another view of the same embodiment as FIG. 8 and FIG. 9. In the view provided by FIG. 10, a portion of housing 220 is shown cut away to reveal shaft 160 within. As can be seen from FIG. 10, an inner clearance 1010, analogous to third clearance 310 in FIG. 3, can be provided between a casing of camera 250 and cleaning head 110. The inner clearance 1010 may be approximately circular.

FIG. 10 also shows a plurality of LEDs 410, which may serve to illuminate the field of view of camera 250. The same variations and modifications discussed above with reference to FIG. 4 may similarly be applied with respect to the embodiment illustrated in FIG. 10.

Figure 11:
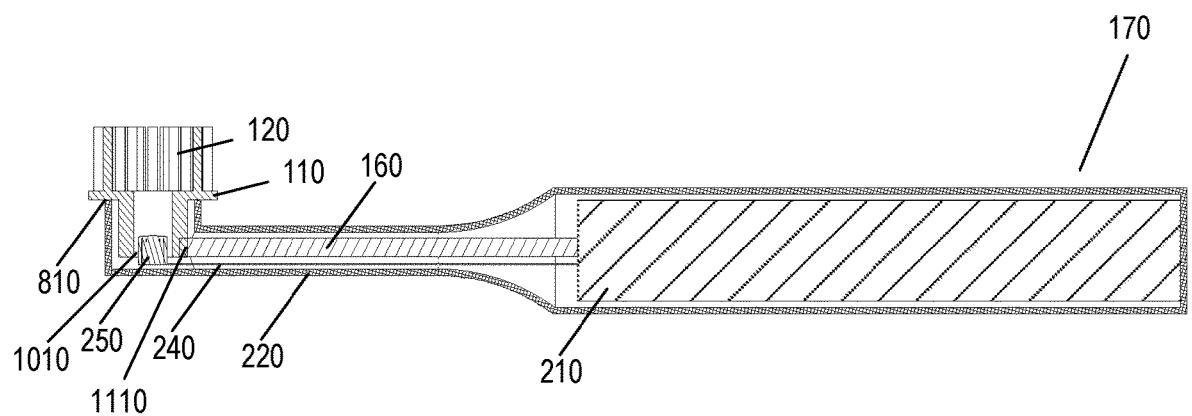
FIG. 11 illustrates a vertical cross-section of a video toothbrush, according to certain embodiments.

FIG. 11 illustrates a vertical cross-section of a video toothbrush according to certain embodiments. The embodiment shown in FIG. 11 may be considered a more complete embodiment similar to those shown in FIGS. 8-10. As shown in FIG. 11, the video toothbrush may include a handle 170.

The handle 170 may include a compartment for motor 210. As in the previously discussed embodiments, shaft 160 may extend from motor 210 to cleaning head 110. In this case, the shaft 160 may provide rotational motion and may transfer rotation to the cleaning head 110 using, for example, gearing at intersection 1110. The rotational motion may be a continuous rotational motion or a reciprocating rotational motion. A camera 250 may be connected with cabling 240, which may be flexible or inflexible power and signal wires.

Inner clearance 1010 can separate the casing of camera 250 from touching the cleaning head 110. Bristles 120 can extend from the surface of cleaning head 110. As can be seen in FIG. 11, outer clearance 810 may be nearly zero, such that the cleaning head 110 can slide or glide over housing 220.

As shown, the camera 250 may be significantly below the level of bristles 120. In other embodiments, the camera may extend higher, such that the camera may, for example, be level with the surface of cleaning head 110.

The handle of the embodiments of FIGS. 1-5 may be similar to the handle of the embodiments of FIGS. 8-11. Thus, the same discussion and modifications mentioned with reference to FIG. 6 may similarly apply to the embodiments of FIGS. 1-5 and 8-11. Likewise, the method shown and described with reference to FIG. 7 may be implemented using the systems shown in FIGS. 1-5 and 8-11.

Other embodiments are also possible. For example, the bristles may be attached to a static portion of the video toothbrush and a plate with holes to accommodate the bristles may be used to move the bristles. In this case, the plate with holes may be referred to as a cleaning head, even though the bristles are the elements actively cleaning teeth. Numerous other modifications and combinations thereof may be applied without departing from the above-identified principles.

Embodiments of the present disclosure may have various benefits and/or advantages. For example, certain embodiments may have a size and shape that are easy to use and have few impacts with teeth other than those being cleaned. Additionally, certain embodiments may have a profile that is smooth and consequently easy to comfortably insert into the user's mouth. Certain embodiments may provide a cleaning head that extends from the head and/or neck of the supporting head. This approach may permit a narrow gap between the cleaning head and the support head. For example, certain embodiments may be stably held against an inside surface of a user's cheek while brushing the outer surface of the teeth, particularly teeth such as molars near the back of the mouth. Certain embodiments may permit a natural adaptation between non-video toothbrush and video toothbrush by providing a form that is a close resemblance to a non-video toothbrush. Certain embodiments may provide a support head and neck that are structurally strong and configured to provide leverage that supports the action of the cleaning head.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. An apparatus, comprising:
a handle comprising an exciter;
a support head extending from a proximal connection with the handle to a distal end;
a camera mounted on the support head near the distal end of the support head;
a shaft extending from the support head and configured to support a cleaning head toward a distal end of the shaft and configured to receive vibration from the exciter toward a proximal end of the shaft; and
the cleaning head comprising a plurality of bristles projecting in a first direction, the cleaning head defining a central opening, wherein the central opening is arranged to provide the camera with a view in the first direction,
wherein the shaft is configured to support the cleaning head with a first clearance between the cleaning head and the support head; and
wherein the support head encloses a portion of the shaft between the handle and the cleaning head, except for a second clearance.

2. The apparatus of claim 1, wherein the first clearance is between 0.5 mm and 5 mm.

3. The apparatus of claim 1, wherein the second clearance is between 0.5 mm and 5 mm.

4. The apparatus of claim 1, wherein the cleaning head is removably attached to the shaft.

5. The apparatus of claim 1, further comprising an LED mounted on the support head and configured to illuminate a field of view of the camera.

6. The apparatus of claim 5, wherein the LED comprises a blue LED or an ultraviolet LED.

7. The apparatus of claim 5, wherein a plurality of additional LEDs are mounted within a casing of the camera and adjacent to a lens of the camera.

8. The apparatus of claim 1, wherein the camera comprises a lens that comprises an outer hydrophilic layer configured to limit fogging.

9. The apparatus of claim 1, wherein the camera comprises a macro lens or a fish-eye lens.

10. The apparatus of claim 1, further comprising a second camera mounted on the support head and configured to operate with the camera to provide a stereoscopic image.

11. The apparatus of claim 1, wherein the exciter comprises an electric motor.

12. The apparatus of claim 11, further comprising:
a battery compartment configured to receive a battery and provided with electrical connections to the electric motor.

13. The apparatus of claim 1, further comprising:
a power button configured to activate the camera and the exciter.

14. The apparatus of claim 1, further comprising:
a communication interface, wherein the communication interface is configured to communicate data between the camera and a remote device.

15. The apparatus of claim 14, wherein the data communicated includes video data and status information for the apparatus.

16. The apparatus of claim 1, wherein the cleaning head is configured to translate with respect to the camera.

17. The apparatus of claim 1, wherein the cleaning head is configured to rotate with respect to the camera.

18. An apparatus, comprising:
a handle comprising an exciter;
a support head extending from a proximal connection with the handle to a distal end;
a camera mounted on the support head near the distal end of the support head; and
a shaft extending from the support head and configured to support a cleaning head toward a distal end of the shaft and configured to receive vibration from the exciter toward a proximal end of the shaft, wherein the shaft is configured to support the cleaning head with a first clearance between the cleaning head and the support head, wherein the camera is configured to view through a central opening of the cleaning head upon installation of the cleaning head; and wherein the support head encloses a portion of the shaft between the handle and the cleaning head, except for a second clearance.

19. The apparatus of claim 18, further comprising a light-emitting diode (LED) mounted on the support head and configured to illuminate a field of view of the camera.

20. The apparatus of claim 19, wherein the LED comprises a blue LED or an ultraviolet LED.

\* \* \* \* \*